United States Patent
Li et al.

(10) Patent No.: US 11,753,621 B2
(45) Date of Patent: Sep. 12, 2023

(54) METHOD FOR CONSTRUCTING FUNCTIONAL EXOSOMES CAPABLE OF EFFICIENTLY LOADING SPECIFIC MIRNA

(71) Applicant: CHINESE PLA GENERAL HOSPITAL, Beijing (CN)

(72) Inventors: Qiankun Li, Beijing (CN); Wenzhi Hu, Beijing (CN); Cuiping Zhang, Beijing (CN); Xiaobing Fu, Beijing (CN)

(73) Assignee: CHINESE PLA GENERAL HOSPITAL, Beijing (CN)

( * ) Notice: Subject to any disclaimer, the term of this patent is extended or adjusted under 35 U.S.C. 154(b) by 0 days.

(21) Appl. No.: 17/520,734

(22) Filed: Nov. 8, 2021

(65) Prior Publication Data

US 2022/0169978 A1 Jun. 2, 2022

(30) Foreign Application Priority Data

Dec. 1, 2020 (CN) .......................... 202011382967.2

(51) Int. Cl.
*C12N 7/00* (2006.01)
*C12N 15/113* (2010.01)
*C12N 15/86* (2006.01)
*C12N 5/073* (2010.01)
*C12N 5/0775* (2010.01)

(52) U.S. Cl.
CPC .......... *C12N 5/0605* (2013.01); *C12N 5/0668* (2013.01); *C12N 7/00* (2013.01); *C12N 15/113* (2013.01); *C12N 15/86* (2013.01); *C12N 2310/141* (2013.01); *C12N 2501/11* (2013.01); *C12N 2501/115* (2013.01); *C12N 2510/00* (2013.01); *C12N 2740/15021* (2013.01); *C12N 2740/15043* (2013.01)

(58) Field of Classification Search
None
See application file for complete search history.

(56) References Cited

U.S. PATENT DOCUMENTS 10,624,849 B2 * 4/2020 Leonard ................ A61K 47/46

OTHER PUBLICATIONS

Pan et al. Development of a microRNA delivery system based on bacteriophage MS2 virus-like particles (2012), FEBS Journal, 279, pp. 1198-1208. (Year: 2012).*

* cited by examiner

*Primary Examiner* — Emily A Cordas
*Assistant Examiner* — Maytee Marie Contes De Jesus
(74) *Attorney, Agent, or Firm* — Muncy, Geissler, Olds & Lowe, P.C.

(57) ABSTRACT

The invention discloses a method for constructing functional exosomes capable of efficiently loading specific miRNA. In order to enable the exosome to carry miRNA with specific regulation function more efficiently so as to play a role in targeted regulation more accurately and efficiently, MS2 phage capsid protein is utilized to edit and construct a capture element of a specific miRNA molecule, and placenta mesenchymal stem cells are reprogrammed to enable the secreted exosome to efficiently load a target miRNA molecule, so that the target miRNA molecule is delivered to tissue cells to play a role in effective regulation, and therefore a new strategy is provided for realizing specific precise treatment in the future.

3 Claims, 7 Drawing Sheets

METHOD FOR CONSTRUCTING FUNCTIONAL EXOSOMES CAPABLE OF EFFICIENTLY LOADING SPECIFIC MIRNA

BACKGROUND OF THE INVENTION

1. Field of the Invention

The invention relates to the field of biomedical materials and cell molecules, in particular to a method for constructing functional exosomes capable of efficiently loading specific miRNA.

2. Description of the Related Art

With the rapid development of cellular molecular therapy, exosomes therapy has become a research hotspot in the field of biomedicine and has received extensive attention. Exosomes are a member of extracellular secretory vesicles, which can be used as transport carriers to carry specific protein and RNA components in the cell. Through fusion to the target cell membrane or endocytosis of the target cell, they deliver RNA and other molecules directly into the target cell to play an effective regulatory role on the recipient cell tissue. Compared with stem cell therapy, stem cell-derived exosomes not only contain a variety of active ingredients secreted by stem cells, but also can avoid transient rejection caused by cell surface antigens of heterogeneous origin, and are safer in clinical treatment applications.

MicroRNA (miRNA) is a type of endogenous small RNA with a length of about 20-24 nucleotides, which has a variety of important regulatory effects in cells. It is speculated that miRNA regulates one-third of human genes and plays a huge role in cell differentiation, biological development, and disease occurrence and development. However, individual miRNA molecules have poor stability in vitro and need to enter cells to play a regulatory role, while exosomes can be used as miRNA carriers to effectively deliver between cells. Due to the limited number of intracellular proteins and RNA carried by exosomes and their complex components, the efficiency of specific action is not high. The previous methods simply used liposome transfection or electrotransfection to overexpress miRNA in cells, and still relied on the self-assembly ability of exosomes to carry miRNA molecules, and the loading efficiency was still limited.

SUMMARY OF THE INVENTION

In view of the shortcomings of the prior art, the invention aims to provide a method for constructing functional exosomes capable of efficiently loading specific miRNA.

In order to achieve the above objective, the invention adopts the following technical solutions:

a method for constructing functional exosomes capable of efficiently loading specific miRNA, comprising the following steps:

S1. using the MS2 phage capsid protein to connect the MS2 protein coding gene to the C1C2 domain in the exosomes Lactadherin protein to construct a C1C2-MS2 (CM) lentiviral plasmid;

S2. connecting the site pac protein used for riveting with MS2 to the target miRNA to construct a pac-miRNA-pac (p-miRNA-p) lentiviral plasmid, both ends of which have pac sites that bind to MS2;

S3. packaging the two plasmids obtained in step S1 and step S2 into lentivirus-infected mesenchymal stem cells; obtaining a confirmed stable transgenic line through screening of resistant drugs; saving the stem cell supernatant, and extracting the exosomes by ultracentrifugation.

Further, the specific process of step S3 is:

S3.1 packaging the C1C2-MS2 lentiviral plasmid and pac-miRNA-pac lentiviral plasmid respectively with a three-plasmid lentiviral packaging system by transfecting 293T cells to obtain CM lentivirus and p-miRNA-p lentivirus;

S3.2. under aseptic conditions, adding placental chorion-derived mesenchymal stem cells (PMSCs) to the stem cell culture medium and incubating them in an incubator at 37° C. and 5% $CO_2$ volume fraction; the stem cell culture medium contains 10% fetal bovine serum by mass;

S3.3. infecting PMSCs with CM lentivirus; using the medium containing 1.0 ug/mL of puromycin for drug screening after 48 hours; obtaining cell line CM-PMSCs stably expressing MS2 after 10-14 days;

S3.4. infecting CM-PMSCs further with p-miRNA-p lentivirus; using the medium containing 600 μg/mL of G418 for drug screening after 48 hours; obtaining the cell line CM-miRNA-PMSCs stably expressing the target miRNA after 2 weeks;

S3.5. incubating CM-miRNA-PMSCs with stem cell culture medium containing 10% by mass of exosome-free serum; collecting the cell supernatant after 24-48 hours; after concentrating by ultrafiltration, obtaining the exosomes CM-miRNA-Exo capable of efficiently loading the target miRNA through the ultracentrifugation method and the exosomes extraction kit.

Further, in step S3.2, the stem cell culture medium is prepared by high-sugar DMEM and DMEM-F12 in a volume ratio of 1:1, and contains 100 U/mL of penicillin, 10 ng/mL of fibroblast growth factor and 10 ng/mL of epidermal growth factor.

The advantageous effects of the invention are: in order to enable the exosome to carry miRNA with the specific regulation function more efficiently so as to play a role in targeted regulation more accurately and efficiently, MS2 phage capsid protein is utilized to edit and construct a capture element of a specific miRNA molecule, and placenta mesenchymal stem cells are reprogrammed to enable the secreted exosome to efficiently load a target miRNA molecule, so that the target miRNA molecule is delivered to tissue cells to play a role in effective regulation, and therefore a new strategy is provided for realizing specific precise treatment in the future.

DETAILED DESCRIPTION OF THE PREFERRED EMBODIMENTS

Figure 1A:
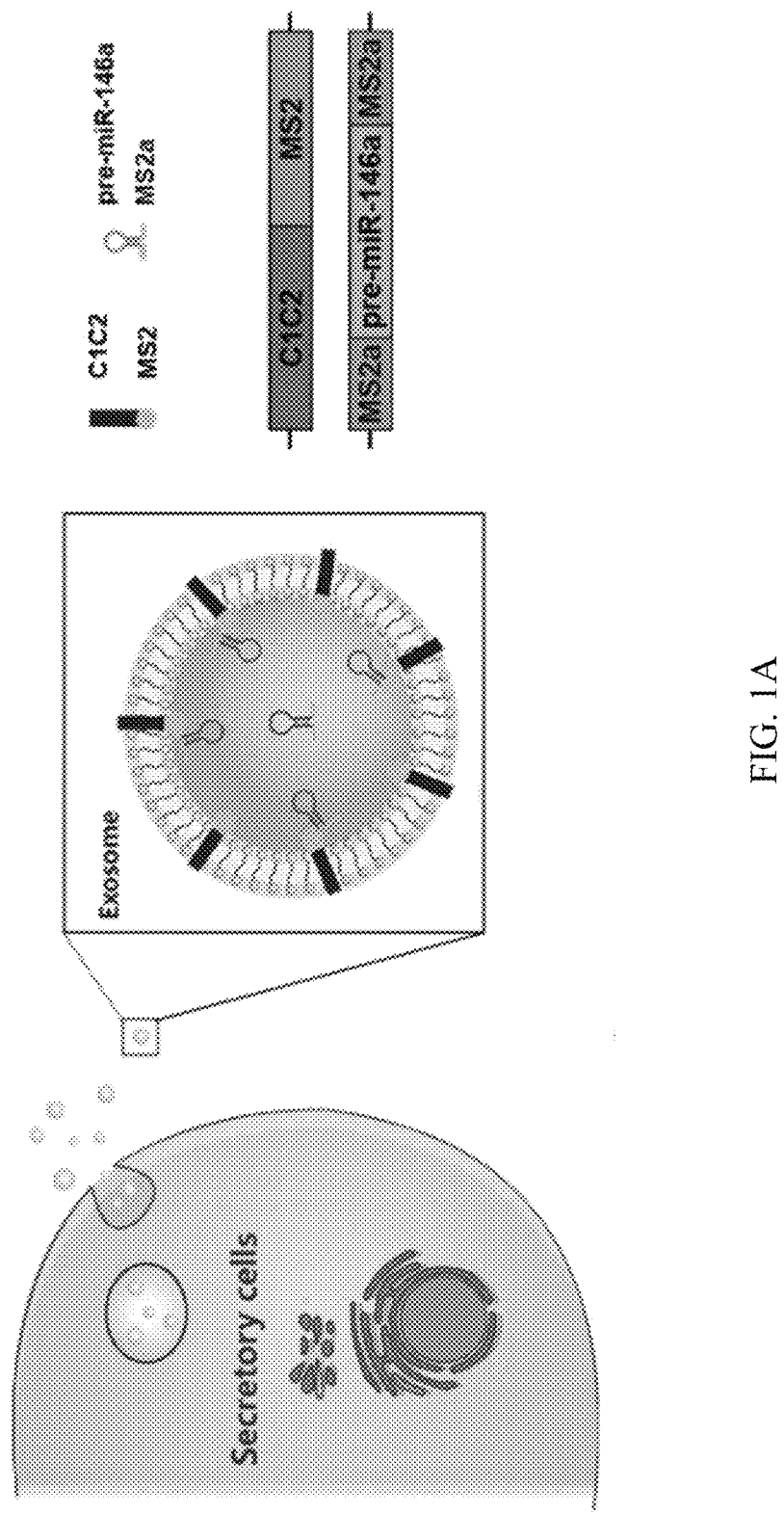
FIG. 1 is a schematic diagram of the construction of the engineered exosomes for highly expressing miR-146a in Embodiment 2 of the invention.

The invention will be further described hereinafter with reference to the drawings. It should be noted that the embodiment is based on the technical solution as a prerequisite, and provides detailed implementation and specific operation procedures, but the protection scope of the invention is not limited to the embodiment.

Embodiment 1

A method for constructing functional exosomes capable of efficiently loading specific miRNA, comprising the following steps:

S1. using the MS2 phage capsid protein to connect the MS2 protein coding gene to the C1C2 domain in the exosomes Lactadherin protein to construct a C1C2-MS2 (CM) lentiviral plasmid;

S2. connecting the site pac protein used for riveting with MS2 to the target miRNA to construct a pac-miRNA-pac (p-miRNA-p p-miRNA-p) lentiviral plasmid, both ends of which have pac sites that bind to MS2;

S3. packaging the two plasmids obtained in step S1 and step S2 into lentivirus-infected mesenchymal stem cells; obtaining a confirmed stable transgenic line through screening of resistant drugs; saving the stem cell supernatant, and extracting the exosomes by ultracentrifugation.

Further, the specific process of step S3 is:

S3.1 packaging the C1C2-MS2 lentiviral plasmid and pac-miRNA-pac lentiviral plasmid respectively with a three-plasmid lentiviral packaging system by transfecting 293T cells to obtain CM lentivirus and p-miRNA-p lentivirus;

S3.2. under aseptic conditions, adding placental chorion-derived mesenchymal stem cells (PMSCs) to the stem cell culture medium and incubating them in an incubator at 37° C. and 5% $CO_2$ volume fraction;

S3.3. infecting PMSCs with CM lentivirus; using a medium containing 1.0 ug/mL of puromycin for drug screening after 48 hours; obtaining cell line CM-PMSCs stably expressing MS2 after 10-14 days;

S3.4. infecting CM-PMSCs further with p-miRNA-p lentivirus; using the medium containing 600 μg/mL of G418 for drug screening after 48 hours; obtaining the cell line CM-miRNA-PMSCs stably expressing the target miRNA after 2 weeks;

S3.5. incubating CM-miRNA-PMSCs with stem cell culture medium containing 10% by mass of exosome-free serum; collecting the cell supernatant after 24-48 hours; after concentrating by ultrafiltration, obtaining the exosomes CM-miRNA-Exo capable of efficiently loading the target miRNA through the ultracentrifugation method and the exosomes extraction kit.

Further, in step S3.2, the stem cell culture medium is prepared by high-sugar DMEM and DMEM-F12 in a volume ratio of 1:1, and contains 100 U/mL of penicillin, 10 ng/mL of fibroblast growth factor and 10 ng/mL of epidermal growth factor.

Embodiment 2

The embodiment is based on the method described in Embodiment 1, and provides a method for constructing functional exosomes with anti-inflammatory effects capable of efficiently carrying miRNA-146a.

A large number of studies have shown that miRNA-146a has an important regulatory role in inflammation. IRAK is a classic downstream target gene of miR-146a and a key regulator of the NF-κB pathway. miR-146a can inhibit the activation of the NF-κB pathway by regulating IRAK1. Therefore, the embodiment verifies the anti-inflammatory effect of CM-miR146a functional exosomes (CM-miR146a-Exo) by using engineered exosomes to act on epidermal cells to detect the expression level of IRAK1 in epidermal cells, observes the healing effect of CM-miR146a-Exo on inflammatory wounds of diabetic mice, and analyzes the differential gene expression and related inflammatory proteins and signal pathways by sequencing the transcriptome of the wound tissue.

The specific process is as follows:

1. constructing pac-pre-miR-146a-pac lentiviral plasmid: querying the gene sequence of miR-146a precursor, constructing the pre-miR-146a lentiviral plasmid of miRNA-146a, with a set of pac anchor sites that bind to MS2 on each side, forming the pac-pre-miR-146a-pac (p-miR146a-p) lentiviral plasmid, as shown in FIG. 1A. FIG. 1A is a schematic diagram of the construction of engineered exosomes: through CM and p-miR146a-p lentiviral plasmid gene reprogramming, stem cell-derived exosomes can efficiently carry miR-146a targeting regulatory molecules.

2. Culturing 293T cells to package lentivirus: collecting 293T cells by trypsinization, and spreading the cells on a 35 mm petri dish with appropriate complete medium to make the cell fusion area reach more than 80% of the total area of the petri dish. Placing the cells in a 37° C. incubator containing 5% $CO_2$ and incubating for 8-24 hours. When the cells are fully attached, transfection can be started. Changing the medium 2 hours before transfection.

3. Packaging p-miR146a-p lentivirus: using the three-plasmid system to transfect the p-miR146a-p lentiviral plasmid and the viral packaging plasmid Mix: 1 μg/μl. (Mix=pMDL: VSV-G: REV=5:3:2) into 293T cells via lipo3000. Removing the plasmid transfection medium after 6 hours, adding 2.5 mL of complete medium preheated at 37° C., and continuing to incubate the cells in an incubator.

4. Collecting the supernatant of p-miR146a-p lentivirus: collecting the lentivirus-containing supernatant after 48 hours and centrifuging at 1500 rpm for 5 minutes. Generally, 2 mL of the lentivirus supernatant can be collected, which can be directly used for the infection of exosome secretory cells, or stored at −80° C. after aliquoting.

5. p-miR146a-p lentivirus infecting: spreading CM-PMSCs (obtained according to the method in Embodiment 1) on a 6-well plate with the best density of 30%-70%. Adding the collected p-miR146a-p lentiviral supernatant to infect CM-PMSCs, and changing to normal stem cell culture medium after 12 hours. Adding culture medium containing 600 μg/mL of G418 after 48 hours to screen the cells for drugs. Obtaining a cell line stably expressing miR-146a (CM-miR146a-PMSCs) after 2 weeks.

Figure 1B:
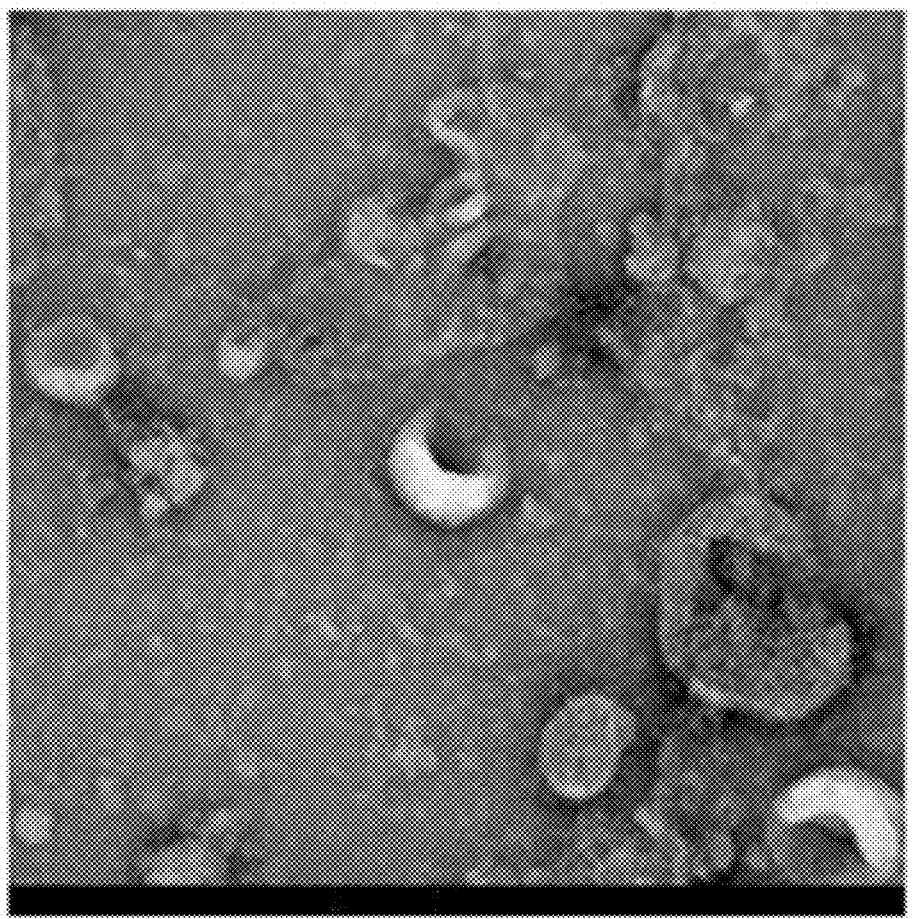
Figure 1C:
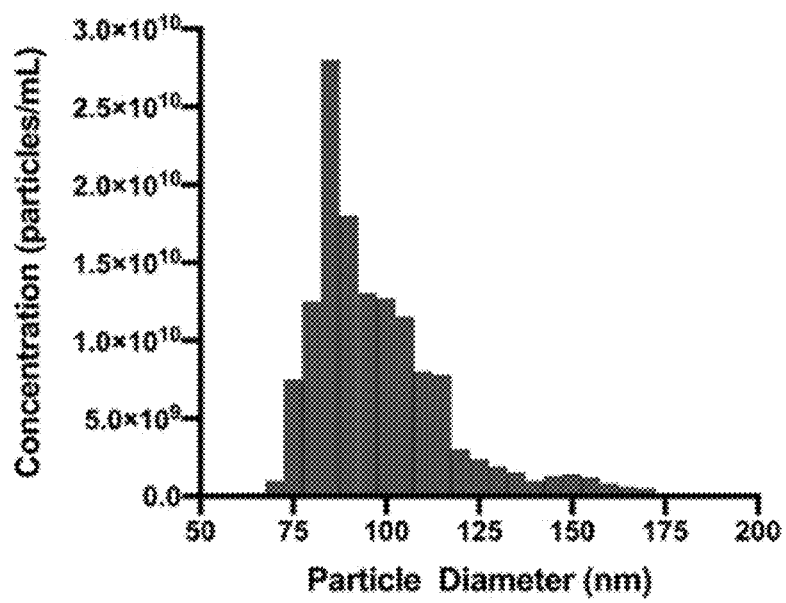
Figure 1D:
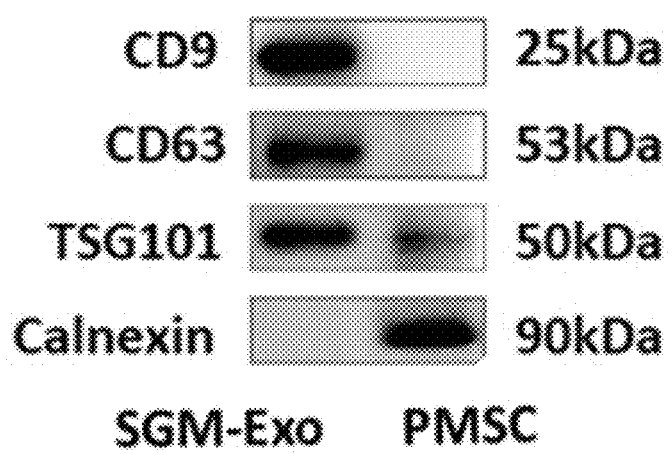

6. Extracting exosomes that highly express miR-146a: incubating CM-miR146a-PMSCs with 10% exosome serum-free stem cell culture medium, collecting the cell supernatant after 24-48 hours, concentrating by ultrafiltration, and using an ultracentrifugation method with an exosome extraction kit to obtain exosomes CM-miR146a-Exo that highly express miR-146a. Observing the morphology of engineered exosomes derived from placental mesenchymal stem cells, and analyzing the size of the exosomes (as shown in FIGS. 1B and 1C). It can be seen from FIG. 1B that the engineered exosomes derived from placental mesenchymal stem cells observed by transmission electron microscopy were disc-shaped vesicles. It can be seen from FIG. 1C that the particle size detection diameter of the engineered exosomes is 70-120 nm. It can be seen from FIG. 1D that the specific marker proteins CD63, CD9, and TSG101 on the surface of exosomes identified by Western blot were positive, and the specific molecule of endoplasmic reticulum Calnexin was negative.

Figure 2A:
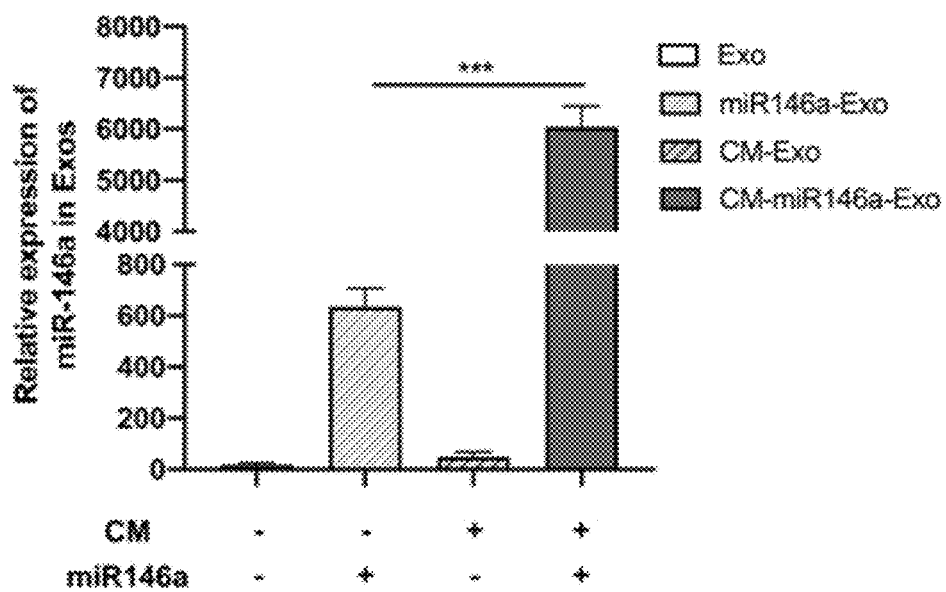
FIG. 2 is a schematic diagram of the loading efficiency and function verification results of CM-miR146a-Exo in Embodiment 2 of the invention.

7. Testing the efficiency of miR-146a loaded with engineered exosomes: using QRT-per to detect the expression of miR-146a in exosomes after miR-146a and CM lentivirus infection of PMSCs. The results showed that the relative expression of miR-146a in the CM-miR146a-Exo group was significantly increased, which was nearly ten times higher than that in the miR146a-Exo group that merely overexpressed miR-146a (as shown in FIG. 2A). It can be seen from FIG. 2 that the relative expression of miR-146a in the CM-miR146a-Exo group increased significantly; compared with the overexpression of miR-146a group, the relative expression of miR-146a increased nearly ten times.

Figure 2B:
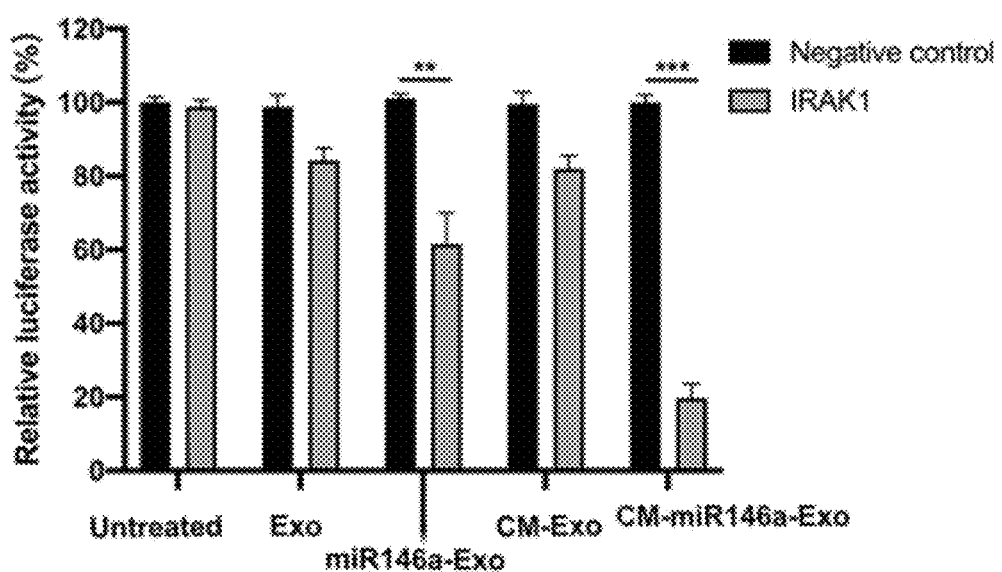

8. Validating targeted anti-inflammatory function of CM-miR146a functional exosomes: miR-146a can inhibit and regulate the downstream target gene IRAK1. IRAK1 is a key regulator of NF-κB pathway, and can inhibit the activation of NF-κB pathway by regulating IRAK1. Through engineered exosomes to act on epidermal cells, using the dual luciferase assay to detect the inhibitory level of miR-146a on the downstream target gene IRAK1, thereby verifying the anti-inflammatory function of exosomes. The results showed that after the exosomes overexpressing miR-146a acted on epidermal cells, the relative fluorescence of IRAK1 decreased by 38%, which had a certain inhibitory effect. The relative fluorescence value of IRAK1 in the cells affected by CM-miR146a-Exo was significantly reduced by 81%, which indicated that CM-miR146a-Exo significantly inhibited the expression of downstream inflammatory factor IRAK1 (as shown in FIG. 2B). It can be seen from FIG. 2B that the dual luciferase experiment showed that the relative fluorescence value of IRAK1 in epidermal cells affected by CM-miR146a-Exo was significantly reduced, which indicated that CM-miR146a-Exo had the most significant inhibitory effect on IRAK1.

Figure 3A:
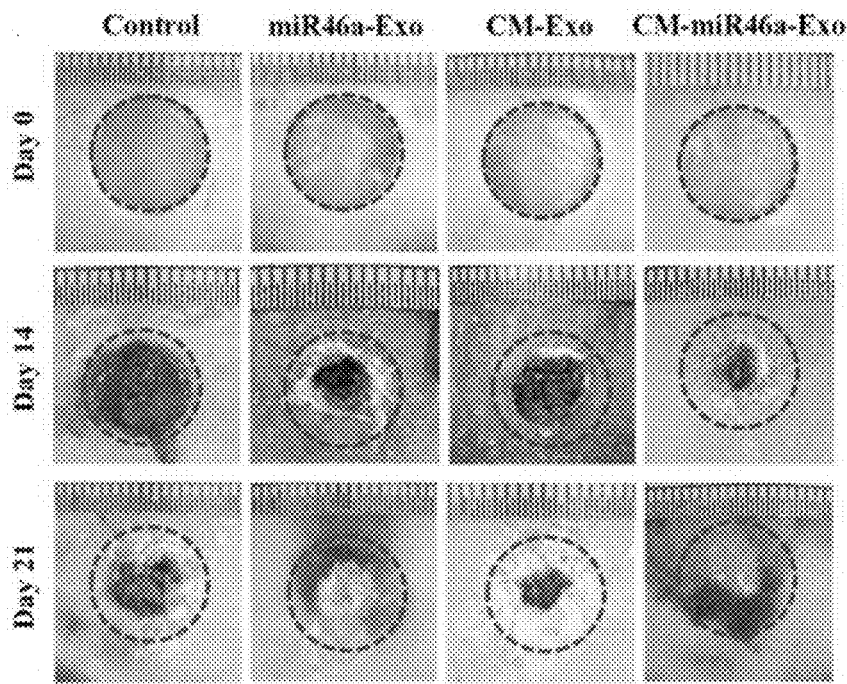
FIG. 3 is a schematic diagram of the results of the effect of CM-miR146a-Exo on wound healing in diabetic mice in Embodiment 2 of the invention.
Figure 3B:
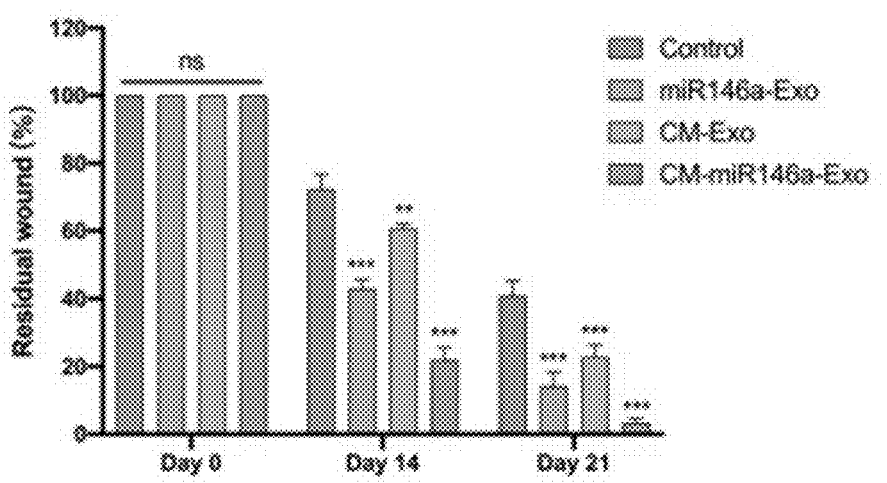
Figure 3C:
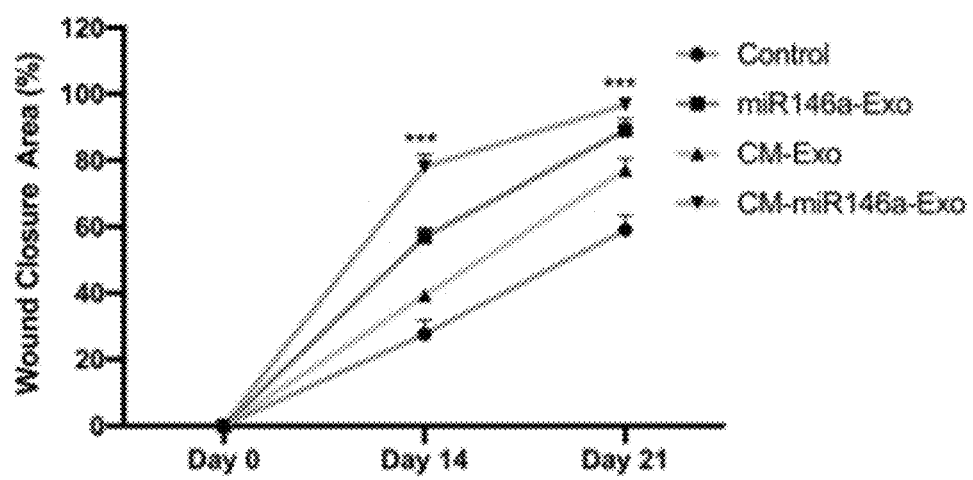

9. The effect of CM-miR146a functional exosomes on inflammatory wounds of diabetic mice: constructing a full-thickness skin wound with a diameter of 1 cm on the back of diabetic mice. Using the blank control group and the different exosomes group on the wounds to observe the wound healing of each group, and statistically analyzing the residual wound area and wound closure rate of each group. The results are shown in FIGS. 3A, B, and C. FIG. 3A shows the general healing of diabetic wounds on the 14th and 21st days. Compared with other control groups, the CM-miR146a-Exo group has a significantly higher wound healing speed, which has the effect of promoting wound repair. Through the statistical analysis of the residual wound area of each group, in FIG. 3B, it is found that the residual wound area of the CM-miR146a-Exo group was significantly smaller than that of the control group during the same period. It can be seen from FIG. 3C that compared with the diabetic wound control group, the CM-miR146a-Exo group has a faster wound healing speed. Wound healing rate= (original wound area-residual wound area)/original wound area×100%.

Figure 4:
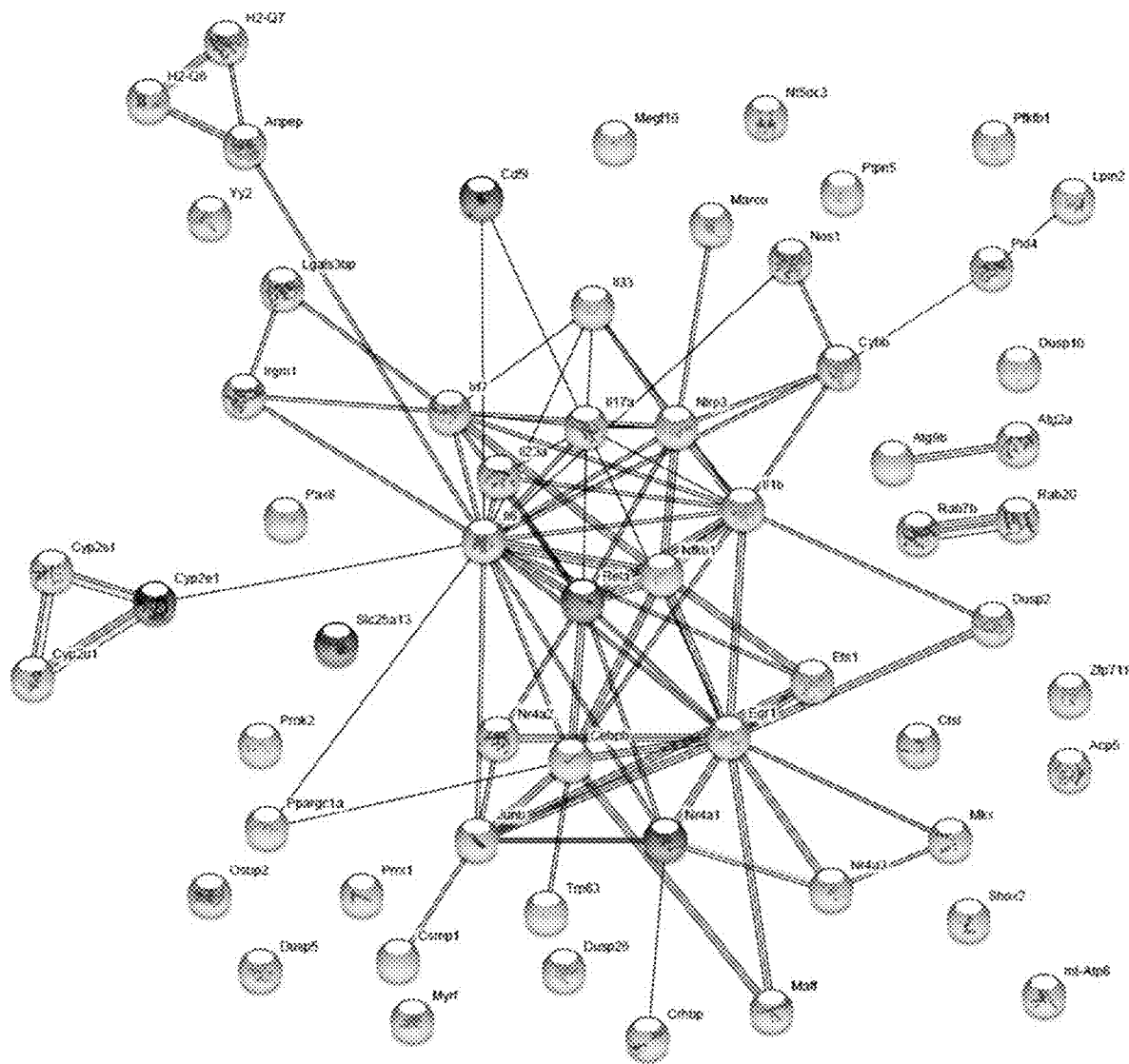
FIG. 4 is a schematic diagram of the inflammation-related protein network analysis of CM-miR146a-Exo acting on transcriptome sequencing of wound tissue in diabetic mice in Embodiment 2 of the invention.

10. Analyzing inflammatory-related proteins of CM-miR146a functional exosomes acting on transcriptome sequencing of diabetic wound tissues: through transcriptome sequencing of wound tissues, analyzing the differential gene expression and related inflammatory proteins and signal pathways involved in regulation. As shown in FIG. 4, the results showed that the expression of inflammatory-related proteins IL-1a, IL-1b, IL-11, TNF, NF-κB1, and Rela decreased in the skin wound tissue treated by CM-miR146a-Exo, and the related inflammatory regulatory pathways were inhibited, which indicated that CM-miR146a functional exosomes have significant anti-inflammatory effects.

For those skilled in the art, various corresponding changes and modifications can be given based on the above technical solutions and concepts, and all these changes and modifications shall all fall within the protection scope of the claims of the invention.

The invention claimed is:

1. A method for constructing functional exosomes capable of efficiently loading specific micro-RNA (miRNA), comprising the following steps:
    S1 connecting a MS2 phage capsid protein to a C1C2 domain in an exosome's Lactadherin protein to construct a C1C2-MS2 (CM) lentiviral plasmid;
    S2 connecting a site pac protein to a target miRNA to construct a pac-miRNA-pac (p-miRNA-p) lentiviral plasmid, wherein the site pac protein is connected to both ends of miRNA to bind MS2;
    S3 packaging the two plasmids obtained in step S1 and step S2 into lentivirus and infecting mesenchymal stem cells with the lentivirus; obtaining a confirmed stable transgenic cell line through screening of resistant drugs; saving the stem cell supernatant; and extracting the exosomes by ultracentrifugation.

2. The method according to claim 1, wherein the specific process of step S3 is:
    S3(1) packaging the C1C2-MS2 lentiviral plasmid and pac-miRNA-pac lentiviral plasmid respectively with a three-plasmid lentiviral packaging system by transfecting 293T cells to obtain CM lentivirus and p-miRNA-p lentivirus;
    S3(2) under aseptic conditions, adding placental chorion-derived mesenchymal stem cells (PMSCs) to a stem cell culture medium and incubating them in an incubator at 37° C. and 5% $CO_2$ volume fraction; the stem cell culture medium contains 10% fetal bovine serum by mass;
    S3(3) infecting PMSCs with the CM lentivirus; using the medium containing 1.0 ug/mL of puromycin for drug screening after 48 hours; obtaining a CM-PMSCs cell line stably expressing MS2 after 10-14 days;
    S3(4) infecting the CM-PMSCs cell line further with the p-miRNA-p lentivirus; using the medium containing 600 μg/mL of G418 for drug screening after 48 hours; obtaining a CM-miRNA-PMSCs cell line stably expressing the target miRNA after 2 weeks;
    S3(5) incubating the CM-miRNA-PMSCs cell line with the stem cell culture medium containing 10% by mass of exosome-free serum; collecting the cell supernatant after 24-48 hours; after concentrating by ultrafiltration, obtaining the exosomes capable of efficiently loading the target miRNA through the ultracentrifugation method and an exosomes extraction kit.

3. The method according to claim 2, wherein in step S3.2, the stem cell culture medium is prepared by high-sugar Dulbecco's Modified Eagle Medium (DMEM) and DMEM-F12 in a volume ratio of 1:1, and contains 100 U/mL of penicillin, 10 ng/mL of fibroblast growth factor and 10 ng/mL of epidermal growth factor.

* * * * *